(12) United States Patent
Falkowski et al.

(10) Patent No.: US 7,107,828 B2
(45) Date of Patent: Sep. 19, 2006

(54) METHOD AND CODE FOR CONTROLLING ACTUATOR RESPONSIVE TO OIL PRESSURE USING OIL VISCOSITY MEASURE

(75) Inventors: Alan G. Falkowski, Lake Orion, MI (US); Dahai Wang, Rochester Hills, MI (US); Michael A Bonne, Leonard, MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 0 days.

(21) Appl. No.: 11/064,742

(22) Filed: Feb. 24, 2005

(65) Prior Publication Data

US 2006/0185426 A1    Aug. 24, 2006

(51) Int. Cl.
*G01M 19/00*    (2006.01)
(52) U.S. Cl. .................. 73/118.1; 73/116; 73/117.2; 73/117.3
(58) Field of Classification Search ............... 73/116, 73/117.2, 117.3, 118.1
See application file for complete search history.

(56) References Cited

U.S. PATENT DOCUMENTS

| | | | | |
|---|---|---|---|---|
| 4,962,732 A | * | 10/1990 | Inoue et al. | 123/90.16 |
| 6,216,528 B1 | * | 4/2001 | Carrell et al. | 73/54.01 |
| 2004/0060344 A1 | * | 4/2004 | Kauffman et al. | 73/53.01 |
| 2004/0244744 A1 | | 12/2004 | Falkowski et al. | |
| 2004/0244751 A1 | | 12/2004 | Falkowski et al. | |

OTHER PUBLICATIONS

Bates, B.; Dosdall, J. M.; and Smith, D. H.; "Variable Displacement by Engine Valve Control," SAE Paper No. 780145 (New York, NY; 1978).
Mueller, Robert S.; and Uitvlugt, Martin W.; "Valve Selector Hardware," SAE Publication No. 780146 (New York, NY; 1978).
Fukui, Toyoaki; Nakagami, Tatsuro; Endo, Hiroyasu; Katsumoto, Takehiko; and Danno, Yoshiaki; "Mitsubishi Orion-MD—A New Variable Displacement Engine," SAE Paper No. 831007 (New York, NY; 1983).
Hatano, Kiyoshi; Iida, Kazumasa; Higashi, Hirohumi; and Murata, Shinichi; "Development of a New Multi-Mode Variable Valve Timing Engine," SAE Paper No. 930878 (New York, NY; 1993).
McElwee, Mark; and Wakeman, Russell; "A Mechanical Valve System with Variable Lift, Duration, and Phase Using a Moving Pivot," SAE Paper No. 970334 (New York, NY; 1997).
Yacoub, Yasser; and Atkinson, Chris; "Modularity in Spark Ignition Engines: A Review of its Benefits, Implementation and Limitations," SAE Publication No. 982688 (New York, NY; 1998).

(Continued)

*Primary Examiner*—Edward Lefkowitz
*Assistant Examiner*—Freddie Kirkland, III
(74) *Attorney, Agent, or Firm*—Thomas A. Jurecko

(57) ABSTRACT

A method and code for controlling the operation of a deactivatable valve lifter of an internal combustion engine includes determining an oil viscosity measure based upon an engine oil pressure achieved when the engine is operating at a warm engine idle operating condition; determining a minimum oil temperature for actuator operation based on a comparison of the oil viscosity measure with a stored value representing the oil's nominal viscosity; and enabling actuator operation when an instantaneous oil temperature is not less than the minimum oil temperature.

13 Claims, 2 Drawing Sheets

OTHER PUBLICATIONS

Zheng, Quan; "Characterization of the Dynamic Response of a Cylinder Deactivation Valvetrain System," SAE Publication No. 2001-01-0669 (New York, NY; 2001).

Leone, T.G.; and Pozar, M.; "Fuel Economy Benefit of Cylinder Deactivation—Sensitivity to Vehicle Application and Operating Constraints," SAE Paper No. 2001-01-3591 (New York, NY; 2001).

Patton, Kenneth J.; Sullivan, Aaron M.; Rask, Rodney B.; and Theobald, Mark A.; "Aggregating Technologies for Reduced Fuel Consumption: A Review of the Technical Content in the 2002 National Research Council Report on CAFÉ," SAE Paper No. 2002-01-0628 (New York, NY; 2002).

Falkowski, Alan G.; McElwee, Mark R.; and Bonne, Michael A.; "Design and Development of the Daimlerchrysler 5.7l Hemi Engine Multi-Displacement Cylinder Deactivation System," SAE Publication No. 2004-01-2106 (New York, NY, May 7, 2004).

* cited by examiner

METHOD AND CODE FOR CONTROLLING ACTUATOR RESPONSIVE TO OIL PRESSURE USING OIL VISCOSITY MEASURE

FIELD OF THE INVENTION

The invention relates generally to controlling the operation of an internal combustion engine that includes an actuator that is responsive to a supply of pressurized engine oil, for example, a deactivatable valve train component responsive to a supply of pressurized engine oil under the control of an electrically-operated solenoid valve.

BACKGROUND OF THE INVENTION

The prior art teaches equipping vehicles with "variable displacement," "displacement on demand," or "multiple displacement" internal combustion engines in which one or more cylinders may be selectively "deactivated" or "suppressed," for example, to improve vehicle fuel economy when operating under relatively low-load conditions. Typically, the cylinders are deactivated through use of deactivatable valve train components, such as deactivating valve lifters as disclosed in U.S. patent publication no. US 2004/0244751 A1, in which a supply of pressurized engine oil is selectively delivered from an engine oil gallery to a deactivatable valve lifter through operation of a solenoid valve under the control of an engine control module. Preferably, the engine control module operates the solenoid valve such that the lifter's locking pins are moved between their respective locked and unlocked positions as the lifter's cam lies on the base circle of its corresponding cam surface, thereby minimizing lifter wear and noise. Thus, the triggering of the oil control solenoids is preferably synchronized to either the crankshaft in a pushrod engine, or the cam shaft in an overhead cam engine.

It is also known that, at each engine speed, there is a range of potential solenoid trigger points that produce a proper sequencing of the deactivatable valve train components, with the deactivation triggering window being significantly "wider" than the reactivation window because less time is needed to increase the oil gallery pressure to the relatively-lower unlatching pressure, as opposed to dropping the oil gallery pressure from a relatively-higher sustained pressure down to the latching pressure. It is further known that the viscosity of the oil supplied to the oil gallery has a significant impact on the amount of time required for deactivation, as a more viscous oil will drain more slowly through the solenoid's and/or the actuator's drain passages, so the prior art has sought to delay the enablement of actuator operation until the engine oil is sure to be warm, for example, by enabling actuator operation only after a minimum engine run time has occurred, or a minimum engine coolant temperature has been achieved.

However, such prior art approaches necessarily prevent early utilization of the deactivatable system, for example, to improve vehicle fuel economy, if the instantaneous oil viscosity is otherwise suitable for actuator operation before the timer has run out, or before the minimum engine coolant temperature has been achieved. Further, such prior art approaches do not accommodate changes in the nominal viscosity of the engine's oil over time, as through aging/oil breakdown (shear) or, perhaps, through operator error as may occur when refilling/replacing engine oil with an oil having a different nominal viscosity rating or "grade." It is, therefore, desirable to correlate enablement of an actuator's operation with a measure representing the instantaneous nominal viscosity of the supplied engine oil.

BRIEF SUMMARY OF THE INVENTION

In accordance with an aspect of the invention, a method and associated computer-executable code for controlling an actuator in an internal combustion engine, wherein the actuator is responsive to a supply of pressurized engine oil, includes determining a first threshold value representing a minimum oil temperature for actuator operation based on an oil viscosity measure; determining a first measure representing an instantaneous oil temperature; and enabling actuator operation when the first measure is not less than the first threshold value. Thus, operation of an oil-pressure-responsive actuator, such as deactivatable valve train component, is enabled only after the engine oil temperature has risen above a minimum oil temperature threshold corresponding with the measure of engine oil viscosity.

In accordance with another aspect of the invention, the step of determining the first threshold value representing a minimum oil temperature for actuator operation includes reading one of several stored calibratable values from a lookup table based upon the oil viscosity measure. Preferably, a value representing a higher minimum engine oil temperature is selected as the engine oil's viscosity increases. In this manner, a higher minimum engine oil temperature will be selected if the engine oil's viscosity is nominally higher, as through use of an engine oil in the engine that has a higher viscosity rating.

In accordance with yet another aspect of the invention, in an exemplary embodiment, the fist measure representing an instantaneous oil temperature is advantageously determined either directly by detecting oil temperature, or indirectly by detecting engine coolant temperature.

In accordance with yet another aspect of the invention, in an exemplary embodiment, the oil viscosity measure is advantageously inferred from a detected engine oil pressure when the engine is operating at a selected engine operating condition, for example, a warm engine idle operating condition at a specific crankshaft speed, as determined by the engine controller during an earlier engine operating cycle. It will be appreciated that the invention alternatively contemplates use of an oil viscosity sensor with which to obtain an instantaneous measure of the engine oil's viscosity, for use in determining the first minimum oil temperature threshold value.

Further, under yet another aspect of the invention, it will be appreciated that, upon determining an instantaneous measure of oil viscosity based, for example, on a detected engine oil pressure and engine speed, as through use of a lookup table containing calibratable values for oil viscosity under perhaps a wide range of engine operating conditions, an alternative method and associated computer-executable code for controlling the oil-pressure-responsive actuator need not determined a minimum oil temperature threshold; rather, the method and code need only directly compare the instantaneous oil viscosity measure to a maximum oil viscosity threshold value, and enable actuator operation only if the instantaneous oil viscosity measure is not greater than the maximum oil viscosity threshold value. Enabling actuator operation based upon a comparison of the inferred instantaneous oil viscosity measure and the correlative maximum oil viscosity threshold similarly advantageously enables actuator operation as soon as the oil's viscosity is at or below the maximum oil viscosity and, further, inherently accommodates circumstances under which the nominal viscosity of the oil is higher than intended, as when an oil having a nominally higher viscosity rating is used in the engine.

Other objects, features, and advantages of the present invention will be readily appreciated upon a review of the subsequent description of the preferred embodiment and the appended claims, taken in conjunction with the accompanying Drawings.

DETAILED DESCRIPTION OF THE INVENTION

Figure 1:
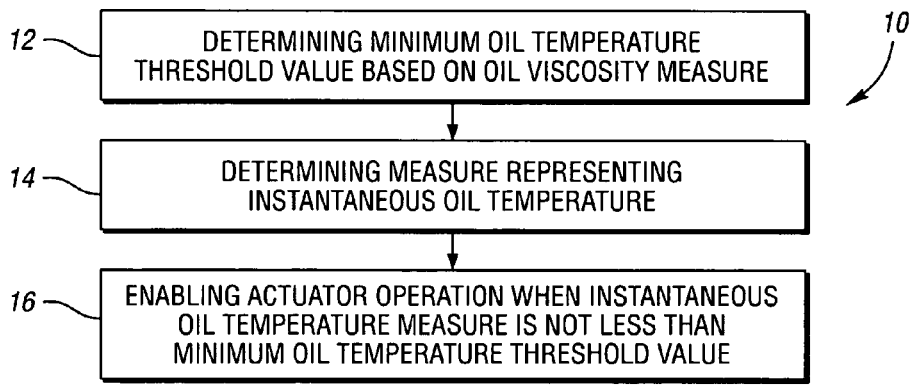
FIG. 1 is a flow chart illustrating the main steps of an exemplary method for controlling the operation of an oil-pressure-responsive actuator of an internal combustion engine, such as a deactivatable valve lifter, in accordance with the invention.

Referring to FIG. 1, a method 10 for controlling the operation of an oil-pressure-responsive actuator of an internal combustion engine, such as a deactivatable valve lifter as disclosed in U.S. patent publication no. US 2004/0244751 A1, the teachings of which are hereby incorporated by reference, generally includes determining, at block 12, a threshold value representing a minimum oil temperature for actuator operation based on an oil viscosity measure; and determining, at block 14, a first measure representing an instantaneous oil temperature. At block 16, actuator operation is enabled when the first measure representing the instantaneous engine oil temperature is not less than the minimum oil temperature threshold value. Thus, the operation of the deactivatable valve lifter is advantageously enabled only after the engine oil temperature measure has risen above the minimum oil temperature threshold corresponding with the measure of the engine oil's viscosity.

Figure 2:
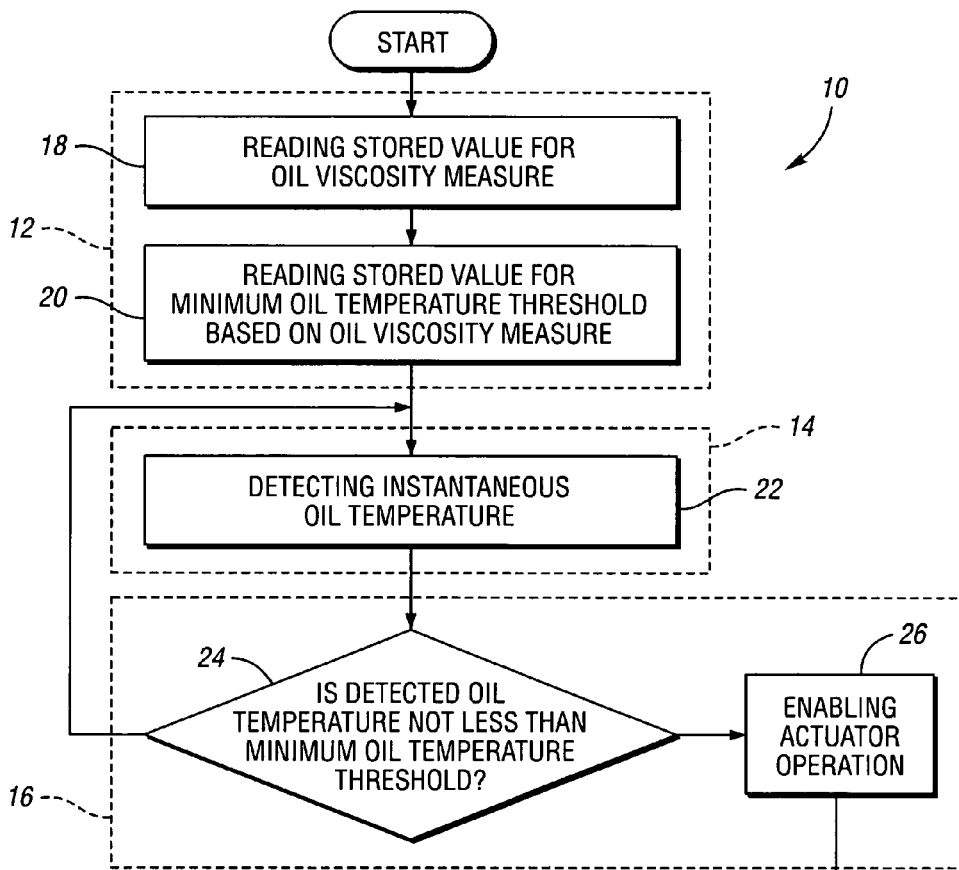
FIG. 2 is a flow chart illustrating in detail the steps of the exemplary method of FIG. 1.

As seen in FIG. 2, the exemplary method 10 for controlling the operation of a deactivatable valve lifter, as stored as computer-executable code in a computer-readable storage medium for use by an engine controller (not shown), more particularly includes, at block 18, reading from a previously-stored value representing the nominal viscosity of the oil to be supplied to the lifter's oil gallery. At block 20, based upon the oil viscosity measure, a previously-stored value for the minimum oil temperature threshold is read from a lookup table containing a plurality of stored values, wherein each stored value represents a predetermined minimum oil temperature to be achieved before enabling lifter operation over a respective range of engine oil viscosities.

The ranges of engine oil viscosities for the stored values for the minimum oil temperature threshold are themselves preferably selected to include oil viscosity values reflecting the aging of the oil, as well as those reflecting the use of grades of oil other than the grade of oil recommended by the vehicle manufacturer. By way of example only, a vehicle manufacturer may specify SAE 5W20 grade oil for use in the engine, whose nominal viscosity might correspond with a nominal minimum oil temperature threshold of perhaps about 20° C.; but, if a vehicle operator inadvertently fills the engine with a higher-viscosity SAE20W50 grade oil when changing the engine's oil, in accordance with one aspect of the invention, the engine controller will determine the greater viscosity of the oil now flowing through the engine as described further below, and select a relatively heightened minimum oil temperature threshold value of perhaps about 50° C. at which to thereafter enable lifter deactivation.

At block 22 of the exemplary method 10, the first measure representing an instantaneous oil temperature is determined by directly detecting the oil temperature with a suitable temperature sensor (not shown). It will be appreciated, however, that if a direct detection of engine oil temperature is not available, the invention alternatively contemplates determining the instantaneous oil temperature measure indirectly, for example, by detecting the engine coolant temperature and inferring the engine oil temperature from the engine coolant temperature, as through use of another lookup table.

At block 24, the instantaneous oil temperature measure is compared to the selected minimum oil temperature threshold value. If the instantaneous oil temperature measure is less than the selected minimum oil temperature threshold value, actuator operation is not yet enabled (for example, as by setting an enable flag to logical zero), and the method loops back to block 26 for another temperature reading. If the instantaneous oil temperature measure is not less than the selected minimum oil temperature threshold value, actuator operation is "enabled" at block 28 (for example, as by setting the enable flag to logical one), whereupon the lifter can be deactivated when the engine controller otherwise determines that suitable engine operating conditions exist for lifter deactivation, such as a low-load cruising operating condition.

Figure 3:
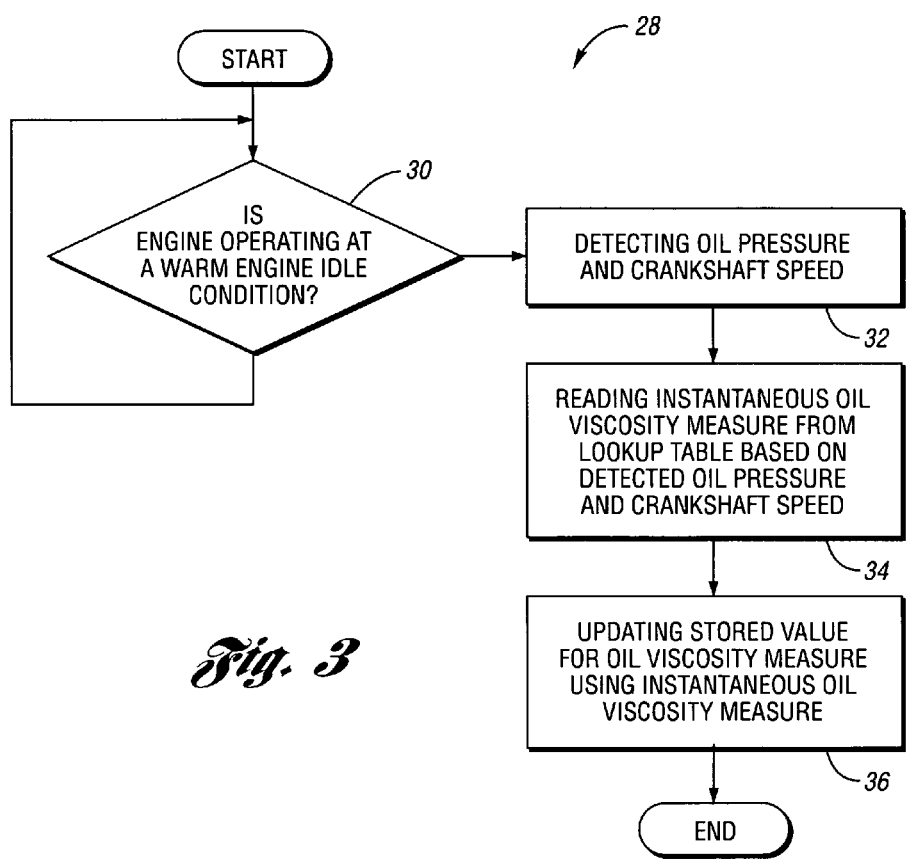
FIG. 3 is a flow chart illustrating in detail the steps whereby a computer-readable storage medium containing a stored value for the oil viscosity measure is updated using a new value inferred from engine oil pressure achieved during a warm engine idle operating condition.

FIG. 3 illustrates an exemplary method 28, in accordance with another aspect of the invention, by which a computer-readable storage medium containing a previously-stored value representing engine oil viscosity is periodically updated using a new value inferred from a detected engine oil pressure achieved during a selected engine operating condition. While the invention contemplates a variety of engine operating conditions during which engine oil pressure may be sampled and normalized, for example, as a function of crankshaft speed (engine RPM) and engine load, a preferred engine operating condition is a warm engine idle operating condition. A further advantage of using a warm engine idle operating condition as the selected operating condition is that is eliminates the need to consider other possible effects on oil pressure at higher engine speeds and loads, such as the potential impact of a pressure relief valve in communication with the one or more engine oil galleries used to deactivate the deactivator lifters.

Thus, at block 30, upon determining that the engine is operating at a warm engine idle, an engine oil pressure when the engine is turning at a target crankshaft speed is detected at block 32, and the detected engine oil pressure and crankshaft speed are used to determine a measure of instantaneous engine oil viscosity. It will be appreciated that the engine oil pressure and crankshaft speed may be sampled and, preferably, filtered during the warm engine idle operating condition, whereupon a two-dimensional lookup table or "surface" can then be used to obtain the desired instantaneous engine oil viscosity measure. The stored value is then suitably updated at block 36 using the determined instantaneous engine oil viscosity measure, for example, using an averaging function.

From the foregoing, it will be appreciated that the invention advantageously allows the engine controller to both enable lifter deactivation earlier than the prior art approaches featuring either a static minimum engine run time or a static (and, necessarily high) minimum oil temperature, while further ensuring that the oil temperature will be sufficiently high to accommodate variation in the nominal viscosity of the engine oil, including those resulting from oil aging/breakdown and the use in the engine of an oil grade other than that specified by the vehicle manufacturer.

While the above description constitutes the preferred embodiment, it will be appreciated that the invention is susceptible to modification, variation and change without departing from the proper scope and fair meaning of the subjoined claims. For example, the invention is equally applicable to mechanical variable valve actuation (VVA) system wherein valve lift, duration, and or phase is adjusted under the control of an engine control module and an engine-oil-responsive actuator. Similarly, the invention is applicable to variable valve timing (VVT) systems employing a "drain and fill" phaser. It will be appreciated that a determination of an oil viscosity measure in accordance with an aspect of the invention may itself be useful as an engine oil quality indicator.

What is claimed is:

1. A method for controlling an actuator in an internal combustion engine, wherein the actuator is responsive to a supply of pressurized engine oil, the method comprising:
   determining a first threshold value representing a minimum oil temperature for actuator operation based on an oil viscosity measure;
   determining a first measure representing an instantaneous oil temperature; and
   enabling actuator operation when the first measure is not less than the first threshold value,
   wherein determining the first threshold value includes selecting a first stored value representing a first predetermined minimum oil temperature when the oil viscosity measure is not greater than a second stored value representing the nominal viscosity of the oil.

2. The method of claim 1, wherein determining includes reading the first threshold value from a lookup table based upon the oil viscosity measure.

3. The method of claim 1, wherein determining the first threshold value includes selecting a third stored value representing a second predetermined minimum oil temperature when the first measure is greater than the first stored value, the second predetermined minimum oil temperature being greater than the first predetermined minimum oil temperature.

4. The method of claim 1, wherein determining the first measure is based upon a detected oil temperature.

5. The method of claim 1, wherein determining the first measure is based upon a detected engine coolant temperature.

6. A method for controlling an actuator in an internal combustion engine, wherein the actuator is responsive to a supply of pressurized oil having a nominal viscosity when the engine is operating at a warm engine idle condition, the method comprising:
   determining an oil viscosity measure based upon an engine oil pressure achieved when the engine is operating at the selected engine operating condition;
   determining a minimum oil temperature for actuator operation based on a comparison of the oil viscosity measure with the nominal viscosity; and
   enabling actuator operation when an instantaneous oil temperature is not less than the minimum oil temperature,
   wherein determining the minimum oil temperature includes selecting a first stored value representing a first predetermined minimum oil temperature when the oil viscosity measure is not greater than the nominal viscosity.

7. The method of claim 6, wherein determining the oil viscosity measure includes detecting an instantaneous engine oil pressure.

8. The method of claim 6, wherein determining the minimum oil temperature includes selecting a second stored value representing a second predetermined minimum oil temperature, higher than the first predetermined minimum oil temperature, when the oil viscosity measure is greater than the first stored value.

9. The method of claim 6, further including adapting a stored value representing the nominal viscosity based on the oil viscosity measure.

10. A computer-readable storage medium including computer executable code for controlling an internal combustion engine having an actuator responsive to a supply of pressurized oil, wherein the storage medium includes:
   code for determining an oil viscosity measure representing an instantaneous viscosity of the supply of pressurized oil;
   code for determining a first threshold value representing a minimum oil temperature for actuator operation based on the oil viscosity measure;
   code for determining a first measure representing an instantaneous oil temperature;
   code for enabling actuator operation when the first measure is not less than the first threshold value; and
   code for selecting a first stored value representing a first predetermined minimum oil temperature when the oil viscosity measure is not greater than a reference oil viscosity value, and code for selecting a second stored value representing a second predetermined minimum oil temperature when the oil viscosity measure is greater than the reference oil viscosity value, the second predetermined minimum oil temperature being wherein than the first predetermined minimum oil temperature.

11. The storage medium of claim 10, including code for reading the first threshold value from a lookup table based upon the oil viscosity measure.

12. The storage medium of claim 10, wherein the code for determining the oil viscosity measure includes:
   code for detecting an engine oil pressure achieved during engine operation at a selected operating condition; and
   code for determining the oil viscosity measure based upon the detected engine oil pressure.

13. The storage medium of claim 12, further including code for updating the reference viscosity value based on the oil viscosity measure.

* * * * *